United States Patent
Kokin et al.

(10) Patent No.: US 9,765,008 B2
(45) Date of Patent: Sep. 19, 2017

(54) PERFLUOROVINYLOXY POLYETHER CARBOXYLIC ACID ALKALI METAL SALT AND METHOD FOR PRODUCING THE SAME

(71) Applicant: UNIMATEC CO., LTD., Tokyo (JP)

(72) Inventors: Keisuke Kokin, Ibaraki (JP); Mitsuru Maeda, Ibaraki (JP); Daisuke Murai, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 0 days.

(21) Appl. No.: 15/110,579

(22) PCT Filed: Dec. 19, 2014

(86) PCT No.: PCT/JP2014/083709
§ 371 (c)(1),
(2) Date: Jul. 8, 2016

(87) PCT Pub. No.: WO2015/104977
PCT Pub. Date: Jul. 16, 2015

(65) Prior Publication Data
US 2016/0332951 A1    Nov. 17, 2016

(30) Foreign Application Priority Data
Jan. 10, 2014    (JP) .................................. 2014-003434

(51) Int. Cl.
*C07C 59/60*    (2006.01)
*C07C 51/41*    (2006.01)

(52) U.S. Cl.
CPC ............ *C07C 59/60* (2013.01); *C07C 51/412* (2013.01)

(58) Field of Classification Search
CPC combination set(s) only.
See application file for complete search history.

(56) References Cited

U.S. PATENT DOCUMENTS

| | | | |
|---|---|---|---|
| 4,131,740 A | 12/1978 | England | |
| 4,138,426 A | 2/1979 | England | |
| 5,670,593 A | 9/1997 | Araki et al. | |
| 5,804,650 A | 9/1998 | Tsuda et al. | |
| 5,986,150 A | 11/1999 | Araki et al. | |
| 2012/0123031 A1 | 5/2012 | Ishikawa et al. | |

FOREIGN PATENT DOCUMENTS

| | | |
|---|---|---|
| JP | S 60-142943 A | 7/1985 |
| JP | B 60-49176 | 10/1985 |
| JP | B 3-80145 | 12/1991 |
| JP | H 8-67795 | 3/1996 |
| JP | B 3291733 | 3/2002 |
| JP | B 3298321 | 4/2002 |
| JP | 2006-131514 A | 5/2006 |
| JP | 2007-153960 | 6/2007 |
| JP | B 4617833 | 11/2010 |
| JP | 2012-117031 A | 6/2012 |

OTHER PUBLICATIONS

International Preliminary Report on Patentability and Written Opinion from corresponding PCT application No. PCT/JP2014/083709 dated Jul. 21, 2016 (5 pgs).
International Search Report from corresponding PCT application No. PCT/JP2014/083709 dated Mar. 10, 2015 (3 pgs).
Kuniaki Takata, Masahiro Takesue, Yuji Iseki, Toshikatu Sata; *Synthesis of vinyl ether compounds by pyrolysis of dimethyl perfluoro-2,7-dimethyl-3,6-dioxa-1,8-octanedioate*; "Journal of Fluorine Chemistry", 75, 1995, p. 163-167.
Plashkin VS,Zapevalova TB,Zapevalov AY,Selishchev BN, *New Method for Synthesizing Unsaturated Perfluorocarboxylic Acids I II* Zhurnal Organicheskoi Khimii (Russian Journal of Organic Chemistry)—1980.—V. 16, I. 3.—p. 540-543.

*Primary Examiner* — Jafar Parsa
*Assistant Examiner* — Amy C Bonaparte
(74) *Attorney, Agent, or Firm* — Brinks Gilson & Lione

(57) ABSTRACT

A perfluorovinyloxy polyether carboxylic acid alkali metal salt represented by the general formula is provided:

$$CF_2=CF[OCF_2CF(CF_3)]_bO(CF_2)_aO[CF(CF_3)CF_2O]_cCF(CF_3)COOM \quad [I],$$

wherein M is alkali metal, preferably sodium or potassium, a is an integer of 1 to 6, preferably 2, and b+c is an integer of 0 to 6, preferably 0 or 1. This perfluorovinyloxy polyether carboxylic acid alkali metal salt is produced by subjecting a perfluorovinyloxy polyether carboxylic acid alkyl ester represented by the general formula:

$$CF_2=CF[OCF_2CF(CF_3)]_bO(CF_2)_aO[CF(CF_3)CF_2O]_cCF(CF_3)COOR \quad [II],$$

wherein R is an alkyl group having 1 to 12 carbon atoms, a is an integer of 1 to 6, and b+c is an integer of 0 to 6; to hydrolysis or solvolysis in the presence of an alkali metal hydroxide.

7 Claims, No Drawings

PERFLUOROVINYLOXY POLYETHER CARBOXYLIC ACID ALKALI METAL SALT AND METHOD FOR PRODUCING THE SAME

RELATED APPLICATION

This application is a 35 U.S.C. §371 national phase filing of International Patent Application No. PCT/JP2014/083709, filed Dec. 19, 2014, which claims priority under 35 U.S.C. §119 to Japanese Patent Application No. 2014-003434, filed Jan. 10, 2014, the entire disclosure of which is hereby expressly incorporated by reference.

TECHNICAL FIELD

The present invention relates to a perfluorovinyloxy polyether carboxylic acid alkali metal salt and a method for producing the same. More particularly, the present invention relates to a perfluorovinyloxy polyether carboxylic acid alkali metal salt that is used as a novel fluorine based reactive emulsifier (an emulsifier having a polymerizable group), and a method for producing the same.

BACKGROUND ART

Patent Document 1 discloses a method for producing a vinylidene fluoride based polymer aqueous dispersion having a solid matters content of 30 to 60 wt. % and a small particle size, i.e., an average particle size of 200 nm or lower, which is suitable for coating materials, wherein the following compounds are effectively used as fluorine based reactive emulsifiers:

Compound 1: $F_2C=CF(CF_2)_{1-10}COOM$
Compound 2: $F_2C=CF(CF_2CFX)_{1-5}COOM$
Compound 3: $F_2C=CFO(CF_2)_{1-10}COOM$
Compound 4: $F_2C=CFO(CF_2CFXO)_{1-10}CF_2CF_2COOM$
Compound 5: $H_2C=CFCF_2O[CF(CF_3)CF_2O]_{0-10}CF(CF_3)COOM$
Compound 6: $F_2C=CFCF_2O[CF(CF_3)CF_2O]_{1-10}CF(CF_3)COOM$
X: F or $CF_3$ group
M: H, $NH_4$, or alkali metal Compound 1 is synthesized by dechlorination of dichloroperfluoroalkyl carboxylic acid obtained by heating ω-hydro-α,β-dichloroperfluoroalkane at a high temperature in the presence of chlorine or nitrogen oxide. Not only the raw material is difficult to obtain, but also high temperature oxidation is required. Thus, this method is not practical (Non-Patent Document 1).

The method for producing Compound 4 is described in detail in Patent Document 2. The use of sulfur trioxide or tin chloride to obtain alkoxycarbonyl carbonyl fluoride ($ROOCCF_2COF$), which is a starting material, causes a safety problem in the reaction process. Moreover, corrosion-resistant equipment is required; thus, special equipment designs are required.

Compound 5 is obtained using, as a starting material, tetrafluorooxetane, which is obtained by the reaction of tetrafluoroethylene with formaldehyde as shown below, according to the following scheme. However, the process is long, and hydrogen fluoride, and zinc metal used in the dehalogenation reaction cause waste problems. Thus, this method is not industrially advantageous (Patent Document 3).

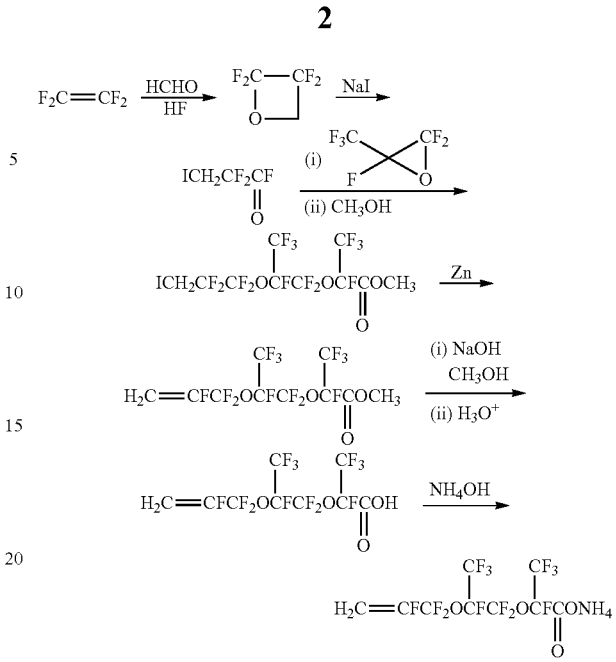

The details of the method for producing Compound 6 of the formula: $CF_2=CFCF_2OCF(CF_3)CF_2OCF(CF_3)COOH$ are unclear. Furthermore, Patent Document 3 discloses a method for obtaining carboxylic acid ammonium and carboxylic acid alkali metal salts via carboxylic acid. However, perfluorovinyl ether is often polymerized even in the presence of acid, such as carboxylic acid, and converted into a polymer. As a result, the yield is reduced. Overall, this method is not suitable as a method for obtaining carboxylic acid metal salts.

PRIOR ART DOCUMENTS

Patent Documents

Patent Document 1: JP-B-3298321
Patent Document 2: JP-B-60-49176
Patent Document 3: JP-B-3291733
Patent Document 4: JP-B-3-80145
Patent Document 5: JP-B-4617833

Non-Patent Documents

Non-Patent Document 1: Zhurnal Organicheskoi Khimll, Vol. 16(3), pp. 540-3 (1980)
Non-Patent Document 2: Fluorine Chem. Vol. 75, pp. 163-167 (1995)

OUTLINE OF THE INVENTION

Problem to be Solved by the Invention

An object of the present invention is to provide a novel compound that does not require special equipment, that uses a readily available raw material as a starting material, and that can be used as a fluorine based reactive emulsifier; and also to provide a method for producing the same.

Means for Solving the Problem

According to the present invention, a perfluorovinyloxy polyether carboxylic acid alkali metal salt represented by the general formula is provided:

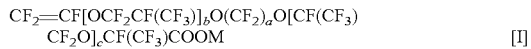
$$CF_2=CF[OCF_2CF(CF_3)]_bO(CF_2)_aO[CF(CF_3)CF_2O]_cCF(CF_3)COOM \quad [I]$$

wherein M is alkali metal, a is an integer of 1 to 6, preferably 2, and b+c is an integer of 0 to 6, preferably 0 or 1. This perfluorovinyloxy polyether carboxylic acid alkali metal salt is produced by subjecting a perfluorovinyloxy polyether carboxylic acid alkyl ester represented by the general formula:

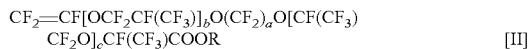
$$CF_2=CF[OCF_2CF(CF_3)]_bO(CF_2)_aO[CF(CF_3)CF_2O]_cCF(CF_3)COOR \quad [II]$$

wherein R is an alkyl group having 1 to 12 carbon atoms, a is an integer of 1 to 6, and b+c is an integer of 0 to 6;
to hydrolysis or solvolysis in the presence of an alkali metal hydroxide.

Effect of the Invention

The perfluorovinyloxy polyether carboxylic acid alkali metal salt of the present invention does not require special equipment, uses a readily available raw material as a starting material, and provides a novel compound that can be used as a fluorine based reactive emulsifier. Therefore, the perfluorovinyloxy polyether carboxylic acid alkali metal salt of the present invention can be effectively used for wide applications, such as crosslinking agents or modifiers for various polymers, anti-reflective films for displays, clad materials of optical fibers, adhesives, various mold release coating agents, surface coating agents, surface modifiers, and water- and oil-repellents.

EMBODIMENTS FOR CARRYING OUT THE INVENTION

The perfluorovinyloxy polyether carboxylic acid alkali metal salt represented by the general formula [I] is produced by hydrolysis or solvolysis of a perfluorovinyloxy polyether carboxylic acid alkyl ester represented by the general formula [II] in the presence of an alkali metal hydroxide.

The perfluorovinyloxy polyether carboxylic acid alkyl ester [II] used as a production raw material of the reaction is produced by reacting a perfluoropolyether dicarboxylic acid dialkyl ester represented by the general formula:

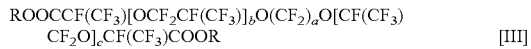
$$ROOCCF(CF_3)[OCF_2CF(CF_3)]_bO(CF_2)_aO[CF(CF_3)CF_2O]_cCF(CF_3)COOR \quad [III]$$

with sodium carbonate, potassium carbonate, or the like, to vinylate one terminal group (Patent Document 4 and Non-Patent Document 2). The perfluoropolyether dicarboxylic acid dialkyl ester [III] is produced by reacting a perfluoropolyether dicarboxylic acid fluoride represented by the general formula:

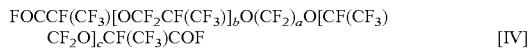
$$FOCCF(CF_3)[OCF_2CF(CF_3)]_bO(CF_2)_aO[CF(CF_3)CF_2O]_cCF(CF_3)COF \quad [IV]$$

in the presence of an aliphatic alcohol having 1 to 12 carbon atoms represented by the general formula ROH, and a metal fluoride, such as sodium fluoride (Patent Document 5).

The hydrolysis or solvolysis of the perfluorovinyloxy polyether carboxylic acid alkyl ester [II] is performed in the presence of an alkali metal hydroxide, and preferably performed at a reaction temperature of about −20 to 0° C. The alkali metal hydroxide is preferably sodium hydroxide or potassium hydroxide, and is suitably selected in view of the reactivity (surface active ability) etc. in the polymerization process. Such an alkali metal hydroxide is used as an aqueous solution or alcohol solution. Any alcohol can be used as long as it can dissolve the alkali metal hydroxide. In terms of handling properties, price, safety, etc., an aliphatic alcohol having 1 to 6 carbon atoms is preferably used, and ethanol or isopropanol is particularly preferably used. Moreover, the alcohol can also be a mixture of methanol, ethanol, and isopropanol. Here, when the reaction temperature is lower than this range, the reaction progresses slowly. In contrast, excessive decomposition proceeds at a high reaction temperature.

The concentration of the alkali metal hydroxide aqueous solution or alcohol solution is not particularly limited. The concentration is preferably about 10 to 20 wt. %, in terms of practical use as a solution. When the solution is dilute, the volume of reaction solutions increases, larger reactors are required, and the amount of waste water increases. In contrast, when the solution has a high concentration, poor stirring may occur due to the deposition of the reaction product. The alkali metal hydroxide is used at a ratio of 0.95 to 1.05 times mol, preferably 0.95 to 1.02 times mol, based on the carboxylic acid ester. When the ratio of the alkali metal hydroxide is greater than this range, excessive decomposition may occur.

The procedure of the reaction is preferably such that an aqueous solution or alcohol solution of the alkali metal hydroxide is added dropwise to an aqueous emulsion (suspension) or alcohol solution of the ester, rather than adding dropwise the ester to the alkali metal hydroxide solution. Moreover, the unreacted carboxylic acid ester is recovered with water or alcohol in the concentration process, and directly reused in the form of a suspension or alcohol solution. Alternatively, the unreacted carboxylic acid ester is reused after isolation and purification by distillation from the suspension or alcohol solution.

The obtained reaction mixture is concentrated by a drying apparatus, such as an evaporator or a conical dryer. However, since the decarboxylation decomposition reaction proceeds at a given temperature or higher, and the yield is reduced, drying is preferably performed under reduced pressure at 120° C. or less.

The perfluorovinyloxy polyether carboxylic acid alkali metal salt of the present invention acts as an emulsifier, for example, in the emulsion polymerization reaction of a fluorine-containing monomer, allowing emulsion polymerization using a less amount of a conventionally used emulsifier or without using such an emulsifier. Further, the perfluorovinyloxy polyether carboxylic acid alkali metal salt of the present invention also acts as a copolymerization component, realizing high vulcanization adhesion, etc.

Examples of the fluorine-containing monomer to be subjected to emulsion polymerization in the presence of the perfluorovinyloxy polyether carboxylic acid alkali metal salt include vinylidene fluoride, tetrafluoroethylene, hexafluoropropylene, chlorotrifluoroethylene, trifluoroethylene, vinyl fluoride, perfluoro(alkyl vinyl ether) containing an alkyl group having 1 to 3 carbon atoms, and the like. One or more of these fluorine-containing monomers are subjected to a polymerization reaction to form a homopolymer or copolymer. These fluorine-containing monomers can also form a copolymer with a fluorine-free monomer, such as propylene or ethylene.

In the polymerization reaction, the perfluorovinyloxy polyether carboxylic acid alkali metal salt is used, optionally together with another known fluorine based emulsifier, as an emulsifier (and a copolymerization component) during the emulsion polymerization reaction at a ratio of about 0.03 to 2 wt. %, preferably about 0.1 to 1 wt. %, based on water or an aqueous medium containing a water-soluble alcohol. The polymerization reaction is preferably performed in the presence of a water-soluble polymerization initiator or a polymerization initiator forming a redox system together with a water-soluble polymerization initiator. The obtained reaction mixture is coagulated through the addition of aqueous solution of a metal salt, such as calcium chloride, followed by water washing and drying. Thus, a homopolymer or copolymer of the desired fluorine-containing monomer can be obtained.

The following describes the present invention with reference to Examples.

EXAMPLE 1

Methyl 2,3,3,3-tetrafluoro-2-[1,1,2,2-tetrafluoro-2-(1,2,2-trifluorovinyloxy)-ethoxy]propanoate of the formula:

$$CF_2=CFO(CF_2)_2OCF(CF_3)COOCH_3 \text{ (a=2, b=0, c=0)}$$

were prepared by a standard method. An ethanol solution (5 ml) of 5.19 g (13.3 mmol) of the above component was cooled to −10° C. or less using ice and salt. Subsequently, an ethanol solution (concentration: 15.8 wt. %) prepared by dissolving potassium hydroxide (purity: 85 wt. %; 0.9 g) in 5 ml of cooled ethanol was slowly added dropwise so that the temperature did not exceed −10° C. Eight hours later, the ethanol was removed by an evaporator. As a result, 4.90 g of wax-like white solid was obtained.

The $^1$H-NMR measurement results showed that the signal indicating methyl ester disappeared. In the $^{19}$F-NMR measurement, the methine signal of —CF(CF$_3$)— shifted. Therefore, it was concluded that potassium 2,3,3,3-tetrafluoro-2-[1,1,2,2-tetrafluoro-2-(1,2,2-trifluorovinyloxy) ethoxy]propanoate was obtained.

$^{19}$F-NMR (CFCl$_3$, CD$_3$OD solvent):
δ(ppm):
−134.75, −134.11 (m, 1F, F$_2$C=C$\underline{F}$—)
−124.53, −124.44 (m, 1F, —C$\underline{F}$CF$_3$—)
−121.82, −121.08 (m, 1F, E-$\underline{F}$C=CF—)
−114.31, −113.77 (m, 1F, Z—$\underline{F}$C=CF—)
−89.28 (s, 2F, =CFOC$\underline{F}_2$—)
−87.08, −83.74 (dd, 2F, —C$\underline{F}_2$OCFCF$_3$—)
−81.22 (s, 3F, —CFC$\underline{F}_3$—)

EXAMPLE 2

Methyl 2,3,3,3-tetrafluoro-2-{1,1,2,3,3,3-hexafluoro-2-[1,1,2,2-tetrafluoro-2-(trifluorovinyloxy)ethoxy]propoxy}propanoate of the formula:

$$CF_2=CFO(CF_2)_2OCF(CF_3)CF_2OCF(CF_3)COOCH_3 \text{ (a=2, b=0, c=1)}$$

and methyl 2,3,3,3-tetrafluoro-2-{1,1,2,2-tetrafluoro-2-[1,2,2,3,3,3-hexafluoro-2-(trifluorovinyloxy)propoxy]ethoxy}propanoate of the formula:

$$CF_2=CFOCF_2CF(CF_3)O(CF_2)_2OCF(CF_3)COOCH_3 \text{ (a=2, b=1, c=0)}$$

were prepared by a standard method. An ethanol solution (8 ml) of 10.8 g (20.0 mmol) of a mixture of the above components was cooled to −10° C. or less using ice and salt. Subsequently, an ethanol solution (concentration: 12.5 wt. %) prepared by dissolving potassium hydroxide (purity: 85 wt. %; 1.32 g) in 10 ml of cooled ethanol was slowly added dropwise so that the temperature did not exceed −10° C. Eight hours later, the ethanol was removed by an evaporator. As a result, 9.88 g of wax-like white solid was obtained.

The $^1$H-NMR measurement results showed that the signal indicating methyl ester disappeared. In the $^{19}$F-NMR measurement, the methine signal of —CF(CF$_3$)— shifted. Therefore, it was concluded that a mixture of potassium 2,3,3,3-tetrafluoro-2-{1,1,2,3,3,3-hexafluoro-2-[1,1,2,2-tetrafluoro-2-(trifluorovinyloxy)ethoxy]propoxy}-propanoate and potassium 2,3,3,3-tetrafluoro-2-{1,1,2,2-tetrafluoro-2-[1,2,2,3,3,3-hexafluoro-2-(trifluorovinyloxy)propoxy]ethoxy}propanoate was obtained.

$^{19}$F-NMR (CFCl$_3$, CD$_3$OD solvent):
δ(ppm):
−144.12, −143.64 (m, 1F, OCF$_2$C$\underline{F}$CF$_3$O—)
−134.75, −134.11 (m, 1F, F$_2$C=C$\underline{F}$—)
−124.53, −124.44 (m, 1F, —C$\underline{F}$CF$_3$—)
−121.82, −121.08 (m, 1F, E-$\underline{F}$C=CF—)
−114.31, −113.77 (m, 1F, Z—$\underline{F}$C=CF—)
−89.30, −88.99 (m, 2F, =CFOC$\underline{F}_2$—)
−86.02, −83.21 (m, 4F, —C$\underline{F}_2$OCFCF$_3$—)
−81.06 (s, 3F, —CFC$\underline{F}_3$CO$_2$—)
−78.90 (s, 3F, —OCF$_2$CFC$\underline{F}_3$—)

REFERENCE EXAMPLE

The following components were charged in a stainless steel pressure vessel (internal volume: 10 L) equipped with a stirring blade.

| | |
|---|---:|
| CF$_3$CF$_2$CF$_2$[OCF(CF$_3$)CF$_2$]OCF(CF$_3$)$_3$COONH$_4$ [emulsifier] | 34 g |
| CF$_2$=CFO(CF$_2$)$_2$OCF(CF$_3$)COOK [reactive emulsifier] | 2.4 g |
| Na$_2$HPO$_4$·12H$_2$O [buffer] | 17 g |
| I(CF$_2$)$_4$I [chain transfer agent] | 27 g |
| Ion exchange water | 5,600 g |

Then, the inside of the vessel was replaced with nitrogen to remove oxygen from the vessel. Further, the following components were charged in the vessel.

| | |
|---|---:|
| Perfluoro(methyl vinyl ether) CF$_2$=CFOCF$_3$ [PMVE] | 790 g |
| Vinylidene fluoride [VdF]/tetrafluoroethylene [TFE] mixed gas (VdF/TFE = 87.5 mol %/12.5 mol %) | 670 g |

The temperature in the vessel was raised to 50° C. When the temperature reached 50° C., the pressure of the vessel was 3.07 MPa·G. After it was confirmed that the temperature was stabilized, 0.8 g of ammonium persulfate and 0.2 g of sodium bisulfite were added as an aqueous solution, and the polymerization reaction was initiated.

After the polymerization reaction proceeded, and when the pressure in the vessel reached 3.00 MPa·G, a monomer mixture having a mixing ratio of VdF/TFE/PMVE=79.6/11.4/9.0 mol % was introduced to raise the pressure to 3.10 MPa·G. The pressure in the vessel was maintained at 3.00 to 3.10 MPa·G during the polymerization reaction by introducing the gases having the above composition.

When the total amount of the introduced gas reached 1,410 g, the addition of the gases was stopped. When the pressure was reduced to 0.20 MPa·G, the vessel was cooled to terminate the polymerization reaction. It took 288 minutes from the supply of the initiator to the end of the polymerization. After completion of the reaction, 8,550 g of fluorine-containing elastomer latex was obtained as a reaction mixture.

The obtained fluorine-containing elastomer latex was put in the same amount of 1 wt. % calcium chloride aqueous solution to coagulate the latex. Then, the coagulated latex was filtered, washed five times with a 5-fold amount of ion exchange water, and dried by a vacuum dryer, thereby obtaining 2,500 g of VdF/TFE/PMVE copolymer. It was confirmed from the $^{19}$F-NMR measurement results that the obtained copolymer had the following composition:

| | |
|---|---|
| VdF | 73.6 mol % |
| TFE | 9.5 mol % |
| PMVE | 16.9 mol % |
| CF$_2$=CFO(CF$_2$)$_2$OCF(CF$_3$)COOK | 0.03 mol % |

The obtained copolymer (100 parts by weight) was compounded with the following components:

| | |
|---|---|
| MT carbon black | 37 parts by weight |
| Triallyl isocyanurate (TAIC WH60, produced by Nippon Kasei Chemical Co., Ltd.) | 4 parts by weight |
| Organic peroxide (Perhexa 25B-40, produced by NOF Corporation) | 1.5 parts by weight |

The mixture was kneaded using an open roll to prepare an unvulcanized compound, followed by press vulcanization at 180° C. for 6 minutes and oven vulcanization at 230° C. for 22 hours. The normal state physical properties (according to JIS K6253 corresponding to ISO 48, and JIS K6251 corresponding to ISO 37) and compression set (according to JIS K6262 corresponding to ISO 815) of the obtained vulcanizate were measured.

Further, the unvulcanized compound before press vulcanization was bonded to a zinc phosphate-treated SPCC steel plate, and press crosslinking was performed at 180° C. for 6 minutes, thereby producing a fluorine-containing elastomer laminated metal plate. The fluorine-containing elastomer laminated metal plate was subjected to a 90 degree peel test (according to JIS K6256 corresponding ISO 813).

Comparative Reference Example 1

In the Reference Example, a VdF/TFE/PMVE copolymer was obtained without using CF$_2$=CFO(CF$_2$)$_2$OCF(CF$_3$)COOK among the emulsifier components.

The following table shows the results obtained in the above Reference Example and Comparative Reference Example 1.

TABLE

| Measurement items | | Ref. Ex. | Comp. Ref. Ex. 1 |
|---|---|---|---|
| Normal state physical properties | | | |
| Hardness | (Duro A) | 75 | 75 |
| 100% modulus | (MPa) | 5.5 | 5.7 |
| Breaking strength | (MPa) | 19.9 | 18.8 |
| Elongation at break | (%) | 250 | 240 |
| Compression set (using a 3.5-mm diameter O ring) | | | |
| 200° C., 22 hr. | (%) | 26 | 25 |
| 200° C., 70 hr. | (%) | 32 | 34 |
| 90 degree peel test | | | |
| Peel strength | (N/mm) | 4.1 | 0.2 |

Comparative Reference Example 2

The surface of a zinc phosphate-treated SPCC steel plate was coated with a solution prepared by dissolving an adhesive comprising aminosilane and vinylsilane as main components (Chemlok AP-133, produced by Lord Corporation) in a 4-fold amount of methyl ethyl ketone. The resultant was dried at room temperature for 30 minutes, followed by baking at 150° C. for 30 minutes. The unvulcanized compound before press vulcanization prepared in Comparative Reference Example 1 was bonded to the adhesive layer-formed metal plate, and press crosslinking was performed at 180° C. for 6 minutes, thereby producing a fluorine-containing elastomer laminated metal plate. The fluorine-containing elastomer laminated metal plate was subjected to a 90 degree peel test in the same manner as mentioned above. As a result, the peel strength was 1.1 (N/mm).

INDUSTRIAL APPLICABILITY

Due to the high polymerization ability, the perfluorovinyloxy polyether carboxylic acid alkali metal salt of the present invention can be effectively used as a crosslinking agent or modifier for various polymers. Further, due to the high fluorine content, various polymers using this metal salt not only have enhanced or improved heat resistance, weather resistance, chemical resistance, and other properties, but also exhibit a low refractive index. Therefore, the perfluorovinyloxy polyether carboxylic acid alkali metal salt of the present invention can also be applied to anti-reflective films for displays, clad materials of optical fibers, etc.

Furthermore, since the terminal carbonyl group is a polar functional group, when the perfluorovinyloxy polyether carboxylic acid alkali metal salt of the present invention is used for adhesive applications, the adhesion to various members can be improved. In addition, due to the surface active properties, the perfluorovinyloxy polyether carboxylic acid alkali metal salt of the present invention can also be used for applications such as various mold release coating agents, surface coating agents, surface modifiers, and water- and oil-repellents.

The invention claimed is:

1. A perfluorovinyloxy polyether carboxylic acid alkali metal salt of the general formula:

$$CF_2=CF[OCF_2CF(CF_3)]_bO(CF_2)_aO[CF(CF_3)CF_2O]_cCF(CF_3)COOM \quad [I]$$

wherein M is alkali metal, a is an integer of 1 to 6, and b+c is an integer of 0 to 6.

2. The perfluorovinyloxy polyether carboxylic acid alkali metal salt according to claim 1, wherein the alkali metal is sodium or potassium, a is 2, and b+c is 0 or 1.

3. A method for producing a perfluorovinyloxy polyether carboxylic acid alkali metal salt of the general formula:

$$CF_2=CF[OCF_2CF(CF_3)]_bO(CF_2)_aO[CF(CF_3)CF_2O]_cCF(CF_3)COOM \quad [I]$$

wherein M is alkali metal, a is an integer of 1 to 6, and b+c is an integer of 0 to 6;

the method comprising subjecting a perfluorovinyloxy polyether carboxylic acid alkyl ester of the general formula:

$$CF_2=CF[OCF_2CF(CF_3)]_bO(CF_2)_aO[CF(CF_3)CF_2O]_cCF(CF_3)COOR \quad [II]$$

wherein R is an alkyl group having 1 to 12 carbon atoms, a is an integer of 1 to 6, and b+c is an integer of 0 to 6;

to hydrolysis or solvolysis in the presence of an alkali metal hydroxide.

4. The method for producing a perfluorovinyloxy polyether carboxylic acid alkali metal salt according to claim 3, wherein the molar ratio of the alkali metal hydroxide to the perfluorovinyloxy polyether carboxylic acid alkyl ester is from 0.95:1 to 1.05:1.

5. The method for producing a perfluorovinyloxy polyether carboxylic acid alkali metal salt according to claim 3, wherein the alkali metal hydroxide is sodium hydroxide or potassium hydroxide.

6. The method for producing a perfluorovinyloxy polyether carboxylic acid alkali metal salt according to claim 3, wherein the solvent used for the solvolysis is an aliphatic alcohol having 1 to 6 carbon atoms.

7. The method for producing a perfluorovinyloxy polyether carboxylic acid alkali metal salt according to claim 3, wherein the hydrolysis or solvolysis is performed by adding dropwise an aqueous solution or alcohol solution of the alkali metal hydroxide into an aqueous emulsion or alcohol solution of the perfluorovinyloxy polyether carboxylic acid alkyl ester.

\* \* \* \* \*